(12) United States Patent
Anderson et al.

(10) Patent No.: US 7,901,385 B2
(45) Date of Patent: Mar. 8, 2011

(54) CASING (75) Inventors: Gregor John McLennan Anderson, Ware (GB); John Mitchell, London (GB)

(73) Assignee: Zogenix, Inc., Emeryville, CA (US)

( * ) Notice: Subject to any disclaimer, the term of this patent is extended or adjusted under 35 U.S.C. 154(b) by 1231 days.

(21) Appl. No.: 10/506,959

(22) PCT Filed: Mar. 18, 2003

(86) PCT No.: PCT/EP03/02876
§ 371 (c)(1),
(2), (4) Date: Sep. 14, 2005

(87) PCT Pub. No.: WO03/077973
PCT Pub. Date: Sep. 25, 2003

(65) Prior Publication Data
US 2006/0069345 A1 Mar. 30, 2006

(30) Foreign Application Priority Data
Mar. 20, 2002 (GB) .................................. 0206560.5

(51) Int. Cl.
A61M 5/315 (2006.01)
(52) U.S. Cl. ........................................ 604/220; 604/68
(58) Field of Classification Search .................... 604/68, 604/220, 232, 69–72, 110, 192–198
See application file for complete search history.

(56) References Cited

U.S. PATENT DOCUMENTS

| 4,596,556 | A | * | 6/1986 | Morrow et al. | 604/70 |
| 4,623,332 | A | * | 11/1986 | Lindmayer et al. | 604/68 |
| 5,499,972 | A | * | 3/1996 | Parsons | 604/68 |
| 5,865,795 | A | * | 2/1999 | Schiff et al. | 604/70 |
| 5,891,086 | A | * | 4/1999 | Weston | 604/70 |
| 6,447,475 | B1 | * | 9/2002 | Castellano | 604/68 |
| 2001/0004681 | A1 | | 6/2001 | Landau | |
| 2001/0004682 | A1 | * | 6/2001 | Weston | 604/72 |
| 2001/0031945 | A1 | * | 10/2001 | Haar et al. | 604/68 |

FOREIGN PATENT DOCUMENTS

| EP | 1 125 593 | 8/2001 |
| JP | 2000-508189 | 7/2000 |
| JP | 2001-224684 | 8/2001 |
| WO | WO 96/24398 | 8/1996 |
| WO | 97/37705 | 10/1997 |
| WO | WO 97/37705 | 10/1997 |

* cited by examiner

Primary Examiner — Nicholas D Lucchesi
Assistant Examiner — Gerald Landry, II
(74) Attorney, Agent, or Firm — Karl Bozicevic; Bozicevic, Field & Francis LLP

(57) ABSTRACT

A casing (50) for an injection device (10) of the type having a safety device which prevents operation of the device (10), incorporating an actuator means (56) by which the safety means of the device (10) can be actuated to allow operation of the device (10). Also a casing (50) for a medicament container having an opening closed prior to use by a break-off tip (135), having relatively moveable first and second casing parts (51, 52), which on relative movement apply a breaking force to the break-off tip (135). A preferred embodiment includes both such features.

29 Claims, 9 Drawing Sheets

CASING

The present invention relates to injection devices, in particular to needle-less injection devices in which a compressed gas cartridge is used to force a jet of medicament through a patient's skin. Specifically, this invention relates to a casing for such an injection device which interacts with the safety and other mechanisms of such an injection device.

Injection devices generally comprise a number of elements. Generally there is a cartridge of a medicament having a nozzle orifice at one end, out of which in the case of a needle-less injection device the medicament is driven under a pressure sufficient to drive it through a patient's skin. Generally there is a drive means to drive the medicament in this manner, typically comprising a plunger moveable within the cartridge toward the nozzle orifice to drive the medicament, and a means to drive the plunger, such as a spring, commonly comprising a spring means such as compressed gas driving a ram which bears upon the plunger. Generally, there is a trigger means operable to cause the drive means to act. Often there is a safety device functioning to prevent the drive means from being inadvertently operated. Such a safety means may function in various ways, for example by obstructing the movement of one or more parts of the injection device which is essential for operation of the device, for example functioning by preventing the trigger means from operating. The cartridge of medicament may for example comprise a dose of liquid or powdered medicament to be administered to the patient. Sometimes in a needle-less injection the nozzle orifice of the cartridge is closed prior to use by a break-off tip. Often the drive means, cartridge is closed prior to use by a break-off tip. Often the drive means, cartridge and orifice lie along an elongate direction which corresponds to the direction along which the plunger moves and the medicament is dispensed.

Needle-less injection devices of various types are described in, inter alia, published International Patent Application Nos. WO-A-93/03779, WO-A-95/03844, WO-A-96/28202 (Weston Medical Limited), U.S. Pat. No. 5,865,795 and U.S. Pat. No. 2001/0004681.

Published International Patent Application No. WO-A-97/37705 (Weston Medical Limited), the contents of which are incorporated herein by reference, discloses a needle-less injection device of the general type described above in which compressed gas in a cylinder 130 drives a ram 111 which bears upon a plunger 104 which is moveable within a medicament cartridge 103 to drive medicament content out through orifice 106. In the device of WO-A-97/37705 operation of the device is prevented by a latch 108 which obstructs the ram 111 and must be moved sideways to allow the ram 111 to move. A trigger means is provided by the device comprising upper 102a and lower 102b relatively moveable sleeve portions, and in its pre-firing configuration the sideways movement of the latch 108 being obstructed by the wall of the upper sleeve 102a. The upper 102a and lower 102b sleeves are moved relative to each other by placing the lower sleeve 102b against the user's skin and urging the upper sleeve downwardly. The relative movement of the upper 102a and lower 102b sleeve portions brings an aperture 139 in the wall of the upper sleeve portion 102a into alignment with the latch 108, allowing the latch to move sideways into the aperture 139 so that it no longer obstructs the ram. A cam surface 109 on the ram 111 bears on the latch 108 under the force exerted by the compressed gas and forces the latch sideways into the aperture 139.

In the device of WO-A-97/37705 a safety mechanism is provided by a tear-off band 137 situated between the upper 102a and lower 102b sleeve portions functioning to obstruct the said relative movement of these sleeve portions until the band 137 has been torn away.

In the device of WO-A-97/37705 the nozzle orifice of the cartridge 103 is closed prior to use by a break-off tip 135 which comprises a seal carrier which carries a seal 134.

However, various problems may arise from the handling and use of a device such as that of WO-A-97/37705 and similar devices. For instance, the device is fragile and may not be robust enough to be transported by a user in, for instance, a handbag or a pocket. Furthermore, the user may perform the steps required for the actuation of the device in the wrong order. The device of WO-A-97/37705 must be actuated by first snapping off the seal carrier 135 and then removing the tear-off band 137, before urging the orifice 106 against the user's skin. If the user mistakenly removes the tear-off band 137 before snapping off the seal carrier 135, it is possible that the action of snapping off the seal carrier may cause the device to be inadvertently actuated. This would result in a wasted dose of the medicament and possibly even delivery of the medicament into the wrong site (e.g. the user's hand).

Also, once the device has been used, the user must dispose of the device and the parts that have been removed, i.e. the seal carrier 135 and the tear-off band 137, in a safe manner so that the user herself or other people, for instance children, are not endangered by loose parts of the actuated device.

Also, in the device of WO-A-97/37705 there is a risk that a weak user may not be able to apply sufficient force to break the break-off seal 135 at the frangible joint 136, or the break-off force may be applied unevenly e.g. resulting in inadequate opening of the orifice 106. Further once the seal carrier 135 has been broken off the user is left in possession of the broken-off carrier 135, potentially with sharp edges around the frangible join 136.

An object of the present invention is to provide a casing in which an injection device, particularly a device such as that of WO-A-97/37705, may be enclosed and which interacts with the device enclosed therein, facilitating the correct operation of the device, and so providing a solution to at least some of the aforementioned problems.

Thus, according to a first aspect the present invention provides a casing for an injection device of the type which comprises a cartridge containing a medicament for injection and having an orifice at one end thereof through which the medicament may be driven for injection through a patient's skin, drive means for driving the medicament through the patient's skin, a trigger means operable to cause the drive means to act, a safety means which in a first configuration prevents the drive means from acting and in a second configuration allows the drive means to act, wherein the casing is adapted to enclose the device, and the casing incorporates an actuator means by which the safety means of an injection device enclosed therein can be brought from its first configuration into its second configuration.

The casing of the present invention facilitates the use of an injection device, in particular in its preferred embodiments by causing the user to operate the injection device according to its pre-determined operating sequence. As secondary advantages the casing can protect the enclosed injection device, improve its aesthetic appearance and improve user compliance by making the injection device appear less intimidating.

Preferably the actuator means may be accessed by a user from outside the casing, so that the user can actuate, i.e. bring from its first configuration into its second configuration, the safety means of an injection device enclosed therein from outside the casing.

In one form for example, the actuator means may have a part exposed to the outside of the casing and accessible to the user, and to which the user may apply operating force to actuate the safety means.

For example such an actuating means may be constructed to bear upon the safety means and thereby apply actuating force to the safety means to bring it from its first configuration into its second configuration.

Herein the term "bear" and derived terms includes all means by which a force applied to one part is communicated to another part, e.g. by pressing to communicate pressure or pulling to communicate tension.

For example the actuator means may comprise a button, tongue or lever which the user may press inwardly to cause the actuator means to bear upon the safety means and thereby bring the safety means from its first configuration into its second configuration.

For example the actuator means, particularly such a button, tongue or lever, may be resiliently connected to the casing such that on application of actuating force to the actuator means, the actuator means operates against the resilient bias.

For example the actuator means may comprise a means to apply a pulling force to the safety means to pull the safety means from its first configuration into its second configuration. For example such an actuator means may comprise a slider, slideably moveable relative to the casing, a connector means connecting the slider to the safety means whereby the user can move the slider to pull the safety means from its first configuration into its second configuration. For example such an actuator means may comprise a pulley wheel, rotatably moveable relative to the casing, a connector means connecting the pulley wheel to the safety means whereby the user can rotate the pulley wheel to pull the safety means from its first configuration into its second configuration.

For example the actuator means may be constructed so that after it has brought the safety means from its first configuration into its second configuration, the actuator means may give a visible or audible (e.g. a "click") indication that this has happened. For example the actuator means may remain locked in a visibly deflected position.

Preferably the casing has retaining means to retain the safety means of an enclosed device in its second configuration after the safety means has been brought from its first configuration into its second configuration.

In another form, for example the actuator means may comprise a window in the casing through which the safety means may be actuated. For example such a window may be so shaped and positioned that a user may be able to reach the safety means of an injection device enclosed therein, or so that a part of or connected to the safety means of an injection device enclosed therein may extend through the window to be accessed and operated by the user from outside of the casing. Such a part may comprise a pull handle or "ripcord" means which may be pulled from outside of the casing to move the safety means from its first configuration into its second configuration.

By "enclosed" is included partial or complete enclosure. As injection devices are generally elongate and cylindrical the casing of the invention will normally be of a generally corresponding shape, e.g. a cylinder or ellipsoid in outer shape. Preferably the casing is adapted to enclose at least the cartridge, the drive means, the trigger means and the safety means of the injection device. Preferably the casing has an opening, which may be removably covered prior to use, by which the orifice through which the medicament may be driven for injection through a patient's skin can be brought adjacent to the patient's skin. In an elongate casing such an opening may be an end opening.

Preferably the casing is adapted to enclose the injection device by being internally shaped to generally conform to the external shape of the device, and/or by the provision of internal supports able to securely hold an injection device enclosed therein. The design of these will depend upon the shape and construction of the injection device to be enclosed. If the casing is to hold a device such as that of WO-A-9737705 which is triggered by being pressed against a user's skin, it is important that the casing is constructed such that pressure applied to the casing to press the device against the user's skin is communicated to the injection device, and such supports may be used to achieve this.

The casing comprises a container for the injection device. The casing may be of single part construction or of multi-part construction for example comprising two or more casing sub-parts which fit together by for example a screw, friction or snap-fit to securely enclose and retain an injection device therein.

A second aspect of the present invention provides a combination of a casing as described above according to the first aspect, and enclosed within the casing an injection device of the type which comprises:

a cartridge containing a medicament for injection and having an orifice at one end thereof through which the medicament may be driven for injection through a patient's skin, drive means for driving the medicament through the patient's skin, a trigger means operable to cause the drive means to act, a safety means which in a first configuration prevents the drive means from acting and in a second configuration allows the drive means to act.

Such a combination comprises:

an injection device of the type which comprises a cartridge containing a medicament for injection and having an orifice at one end thereof through which the medicament may be driven for injection through a patient's skin, drive means for driving the medicament through the patient's skin, a trigger means operable to cause the drive means to act, a safety means which in a first configuration prevents the drive means from acting and in a second configuration allows the drive means to act;

a casing enclosing the injection device, wherein the casing incorporates an actuator means by which the safety means of the injection device enclosed therein can be brought from its first configuration into its second configuration.

The combination of the casing with the injection device already enclosed therein may be provided to a user e.g. a prescription patient, as a unit.

Preferably in its first configuration the safety means prevents the drive means from acting by preventing the trigger means from operating, for example by obstructing the movement of a moveable trigger part, and in its second configuration allows the trigger means to operate.

Therefore preferably the safety means comprises an obstructer part which in the first configuration obstructs, and in the second configuration allows, the movement of a moveable trigger part.

Such a safety means may be moveable, e.g. by displacement and/or deformation, by using the actuator means, from its first configuration to its second configuration, e.g. the actuating means may bear upon the safety means and thereby apply actuating force to the safety means to move it e.g. by displacement and/or deformation.

When the casing is elongate, preferably a moveable safety means comprises an obstructer part which is brought from its first configuration to its second configuration by a movement of the obstructer part e.g. by displacement or deformation, or the entire safety means, in a direction perpendicular to the elongate direction.

For example a moveable safety means may comprise a collar (the term includes a part-collar) shaped to at least partly surround the injection device, and moveable from its first configuration into its second configuration in a direction generally perpendicular to the direction in which the medicament is dispensed, the collar incorporating an obstructer part.

Preferably the safety means, or at least the obstructer part, is biased to be retained in its first configuration and is movable against this bias into its second configuration.

For example a moveable safety means may comprise a removable obstructer part, e.g. a tear-off band functioning as an obstructer part as disclosed in WO-A-97/37750, and such a band may have an extension which is accessible from outside of the casing, e.g. through a window in the casing, which a user may grip and pull to remove the obstructer part from the injection device and from the casing.

Alternatively the safety means may be broken or destroyed in its second configuration, e.g. the actuating means may bear upon the safety means and thereby apply actuating force to the safety means to break or destroy it.

Preferably the injection device is as disclosed in WO-A-97/37705 the content of which is incorporated herein by reference.

Therefore preferably the trigger means, as in WO-A-97/37705, is provided by two relatively moveable upper and lower sleeve parts which on relative movement allow the drive means to act.

When the injection device comprises a device in which the trigger means comprises two relatively moveable upper and lower sleeve parts which on relative movement allow the drive means to act, the safety means may comprise an obstructer part which in its first configuration obstructs, and in its second configuration allows, the relative movement of these sleeve parts.

For example with such a device preferably the safety means comprises an obstructer part which is brought from its first configuration to its second configuration by a movement of the obstructer part in a direction perpendicular to the direction of relative movement of these two sleeves, this direction suitably being perpendicular to the elongate direction of the device and the casing, being also generally perpendicular to the dispensing direction of the medicament.

For example when the injection device comprises a device in which the trigger means comprises two relatively moveable upper and lower sleeve parts which on relative movement allow the drive means to act, as in the device of WO-A-9737705, such a moveable safety means may comprise a collar shaped to at least partly surround the injection device, and moveable from its first configuration into its second configuration in a direction perpendicular to the direction of relative movement of these two sleeves, the collar incorporating an obstructer part which in the first configuration is situated between the two sleeves to obstruct the relative movement, and in the second configuration is displaced in a direction perpendicular to the direction of relative movement of these two sleeves to thereby allow the relative movement of these sleeves.

Such a collar may surround that part of the injection device which is longitudinally between the two sleeves. Such a collar may be resiliently biased into its first configuration, for example by spring parts bearing upon the injection device or upon the casing, so that movement into the second configuration is against this bias.

Preferably the safety means, e.g. a collar as described above, has retaining means by which it may be retained in its second configuration after the safety means has been actuated. Such retaining means may interact, e.g. lock with, corresponding retaining means on the casing or the injection device. The operation of such retaining means may be accompanied by a visible or audible indication thereof.

Alternatively the safety means may require a continuous actuation of the actuator means to retain the safety means in its second configuration.

Such a safety means, e.g. the above described collar, may be integrally made of resilient plastics materials.

A third aspect of the present invention provides a casing adapted to enclose a container of a medicament of the type having an opening at one end through which the medicament may be accessed for dispensing and the opening being closed prior to use by a break-off tip, the casing comprising relatively moveable first and second casing parts, being a first casing part adapted to hold the container, and a second part adapted to bear upon the break-off tip of a container held by the first casing part as a result of such relative motion to apply a force thereto causing the break-off tip to break off from the container.

Preferably the container is an injection device of the type comprising a cartridge having its injection nozzle orifice closed prior to use by a break-off tip, and the casing comprises a container for the device.

The invention also provides a combination of such a casing and an injection device enclosed therein.

Such a combination comprises:

a casing enclosing an injection device of the type comprising a cartridge having its injection nozzle orifice closed prior to use by a break-off tip, the casing comprising relatively moveable first and second casing parts, being a first casing part adapted to hold the injection device, and a second part adapted to bear upon the break-off tip as a result of such relative motion to apply a force thereto causing the break-off tip to break off from the injection device.

In one embodiment the first casing part may be elongated along a longitudinal axis, the first casing part may be adapted hold the container non rotatably relative thereto, e.g. by internal supports and the second part can be moved in rotary motion relative to the first part so as to bear on the break-off tip of a container held by the first casing part, and to apply a twisting shearing force to the frangible joint between the break-off tip and the container.

Such rotary relative motion may be about a rotation axis coaxial with this longitudinal axis, about a rotation axis parallel to but non-coaxial with this longitudinal axis, or about a rotation axis at a non-zero angle to the longitudinal axis. The latter two modes of rotary motion may be advantageous in applying a shearing force to the frangible joint.

For example such rotation may be achieved by means of the first and second casing parts being initially connected together by a screw thread or bayonet connection, so that un-connecting the connection applies a shear force to break off the tip of a container held by the first casing part, and also separates the first and second casing parts to hereby expose the opening for use.

Alternatively such rotary relative motion may be about a rotation axis transverse to e.g. preferably perpendicular to this longitudinal axis so as to snap the frangible joint. For example such rotation may be achieved by the second casing part being pivotally mounted on the first casing part, with a pivot axis perpendicular to the longitudinal axis. Alternatively the second casing part may be hinged to the first casing part about a hinge axis, such that as the second casing part moves in rotary hinged motion about this hinge axis relative to the first casing part the second casing part bears upon the break-off tip.

Alternatively the second casing part may incorporate a bearing part moveable relative to the second casing part and first casing part, e.g. operable by a button or lever etc. of the second casing part, to thereby bear upon the break off tip.

The second casing part may have internal parts to hold or support the break off tip, and/or which bear on the break off tip during the relative motion. The second casing part may be internally provided with gripping means to assist the second casing part in bearing on the break-off tip of a container held by the first casing part, and applying the shearing force. The design of these will depend upon the shape and construction of the injection device to be enclosed.

For example the second casing part may incorporate a cup part having internal surfaces of a rubbery material with a high coefficient of friction relative to the break-off tip.

In a preferred embodiment the casing of this third aspect of the invention is a casing of the first aspect of the invention, which may be used in a combination as in the second aspect of this invention, and the first casing part is adapted to hold an injection device wherein the cartridge has an opening at one end through which the medicament may be dispensed and the opening is closed prior to use by the break-off tip.

This preferred embodiment of the invention therefore comprises;

a casing for an injection device of the type which comprises a cartridge containing a medicament for injection and having an orifice at one end thereof through which the medicament may be driven for injection through a patient's skin, drive means for driving the medicament through the patient's skin, a trigger means operable to cause the drive means to act, a safety means which in a first configuration prevents the drive means from acting and in a second configuration allows the drive means to act, and having its injection nozzle orifice closed prior to use by a break-off tip, wherein:

the casing is adapted to enclose the device, and the casing incorporates an actuator means by which the safety means of an injection device enclosed therein can be brought from its first configuration into its second configuration, and, the casing comprises relatively moveable first and second casing parts, being a first casing part adapted to hold the injection device, and a second part adapted to bear upon the break-off tip as a result of such relative motion to apply a force thereto causing the break-off tip to break off from an injection device enclosed within the casing.

Preferably for use with such an injection device the first casing part may be elongated in the longitudinal direction along which the plunger moves to drive the medicament through the orifice.

Preferably when the first casing part is adapted to hold an injection device the first casing part has an opening by which the orifice through which the medicament may be driven for injection through a patient's skin can be brought adjacent to the patient's skin, and this opening may be an end opening of an elongate first casing part, and the second casing part comprises a removable cover for this end opening, e.g. in the form of an end cap.

In this preferred embodiment, the casing may be constructed so that the actuator means cannot be operated before the second casing part has been moved relative to the first casing part in the manner described above. This can ensure that an injection device contained therein is operated in the correct operating sequence, i.e. the break-off tip is first broken off and only thereafter the drive means can be caused to operate.

For example the second casing part may comprise a cover part over the actuator means which prevents operation of the actuator means until the cover part is removed. For example the second casing part may comprise a cap, covering the actuator, with a screw thread connection to the first casing part and the action of unscrewing such a cap may both break off the break-off tip and expose the actuator for use.

Alternatively the second casing part may incorporate a locking means to lock the actuator means until the second casing part has been removed.

Alternatively the second casing part may comprise the actuator means, so that the movement of the second casing part relative to the first casing part causes the safety means of an injection device enclosed within the casing to move from its first configuration to its second configuration. For example the second casing part may comprise a bearing part which bears upon the safety means, e.g. by pressure or pulling analogous to the description above, to move the safety means from its first configuration to its second configuration.

For example the second casing part may itself comprise a safety means. For example the second casing means may incorporate at least one obstructer part which functions to obstruct movement of a part of the injection device which is essential for operation, and which is moved from a first configuration to a second configuration by the relative movement of the second casing part.

The casing of all aspects of the invention, and the safety means such as a collar, may conveniently be made of plastics materials by for example injection moulding.

The invention also provides a combination of such a casing and an injection device enclosed therein.

Preferred features of such a casing, and its combination with an injection device, are as described above.

The construction and operation of a device according to this invention will now be described by way of example only with reference to the following Figures.

Referring to FIGS. 1-4 the operation of the device 10 disclosed in WO-A-97/37705 is illustrated schematically, the numbering scheme of WO-A-97/37705 being followed in these drawings. The device 10 comprises an upper sleeve part 102*a* and a lower sleeve part 102*b* which are relatively moveable toward each other. At the lower end of the device is a break-off tip 135 which can be broken off at frangible joint 136 as described in WO-A-97/37705 to open a nozzle orifice 106. The action of moving the sleeve parts 102a, 102b in the way described triggers the latch mechanism (108 in WO-A-97/37705, not shown in FIGS. 1-4) and causes compressed gas in cylinder 130 to operate an internal ram (111 in WO-A-97/37705, not shown in FIGS. 1-4) which drives medicament content 105 in cartridge 103 out through orifice 106. However prior to use the relative movement of sleeve parts 102a and 102b is obstructed by tear-off band 137, being a safety means.

Figure 1:
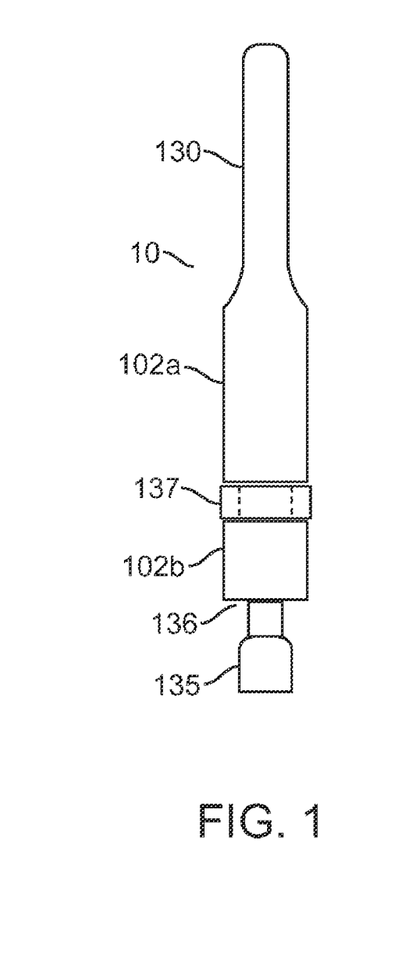
FIGS. 1-4 show schematically the operation of a known type of needle-less injection device.
Figure 2:
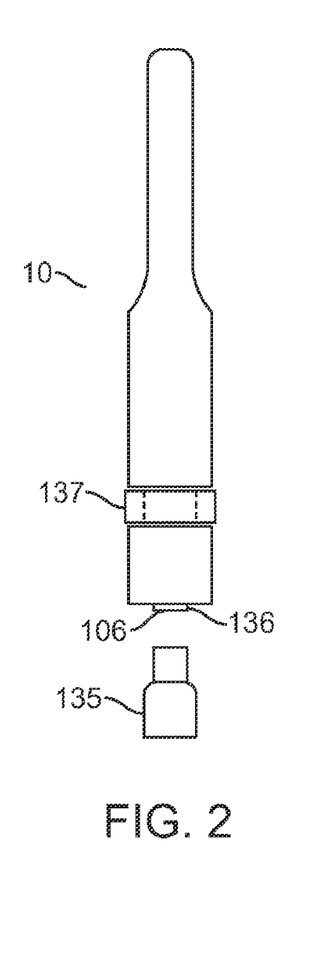
Figure 3:
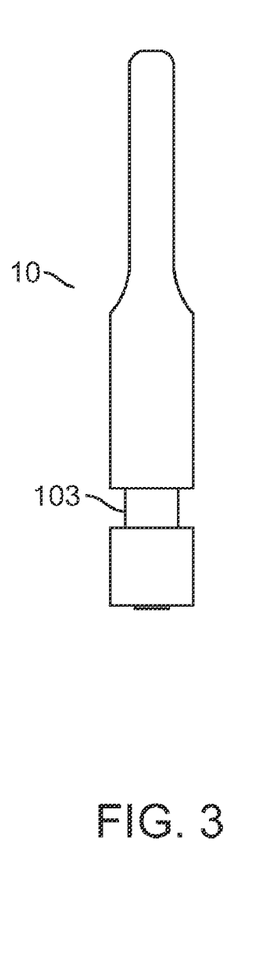
Figure 4:
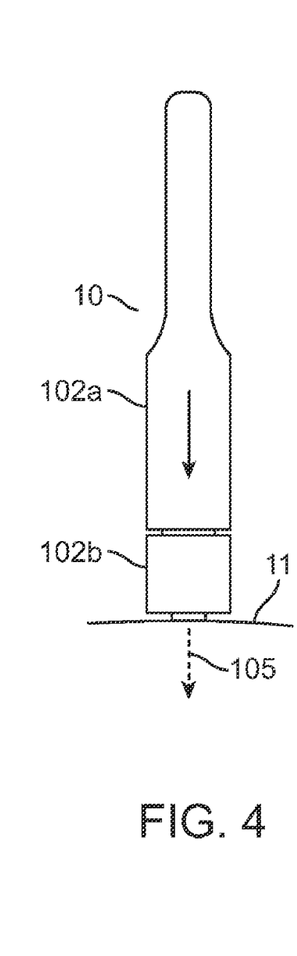

The operation of the device is shown sequentially through FIGS. 1-4. FIG. 1 shows the pre-use configuration with band 137 in place. In FIG. 2 the break-off tip 135 has been broken off at frangible joint 136, exposing orifice 106. In FIG. 3 the tear off band 137 has been torn off so that relative movement of sleeve parts 102a, 102b is no longer obstructed. In FIG. 4 the orifice 106 has been placed against the skin 11 of the user and pressure has been applied to the cylinder 130 to force sleeve part 102a downwardly relative to sleeve part 102b. As described in WO-A-97/37705 this has "fired" the device and caused the medicament 105 to be injected through the user's skin 11.

Referring to FIGS. 5-9 a casing 50 of this invention is shown in a longitudinal sectional view. The casing 50 encloses a device 10 as shown in FIGS. 1-4. The device 10 is an elongate device, the direction of its longitudinal axis being shown by a dashed line. This direction is also the direction along which the sleeve parts 102a, 102b move relative to each other, and the direction in which medicament content is ejected from the orifice 106.

Figure 5:
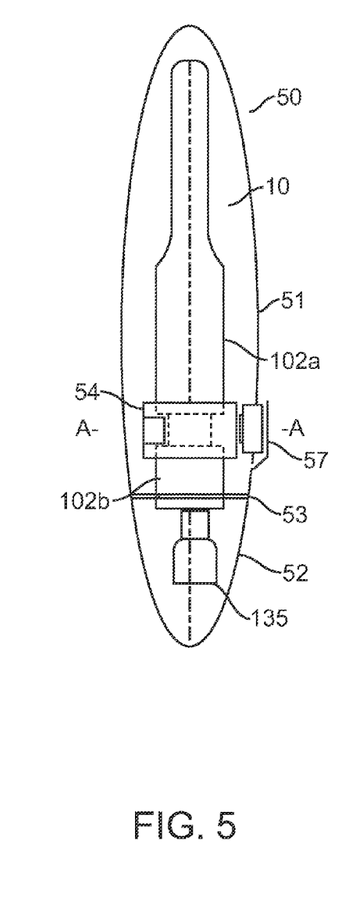
FIGS. 5-8 show schematically the construction of a casing of this invention and its operation with a device as shown in FIGS. 1-4.

The casing 50 is generally ellipsoidal elongate in a direction parallel to the longitudinal axis of the device 10 and comprises a first casing part 51 and a second casing part 52. The first casing part 51 and second casing part 52 are joined at a screw thread connection 53. Each casing part 51, 52 may itself comprise sub-assemblies fitted together. The casing parts 51, 52 are made of plastics material by injection moulding.

Within first casing part 51 the device 10 is supported and held securely by internal supports, bulkheads etc. (not shown but the construction of which will be apparent to those skilled in the art). In particular the device 10 is held within first casing part 51 such that device 10 is non-rotatable relative to part 51 about an axis parallel to the long axis of casing 51, 52.

Figure 9A:
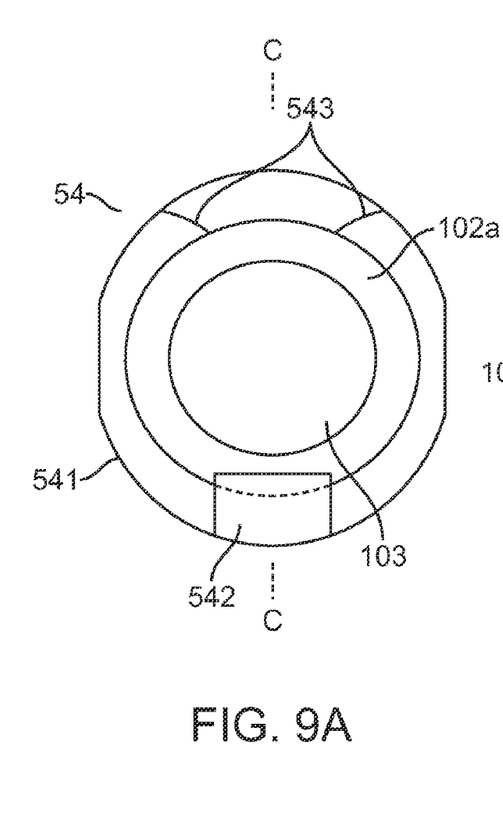
FIG. 9 shows the construction and operation of the safety means as used in the casing of FIGS. 1 to 8.
Figure 9B:
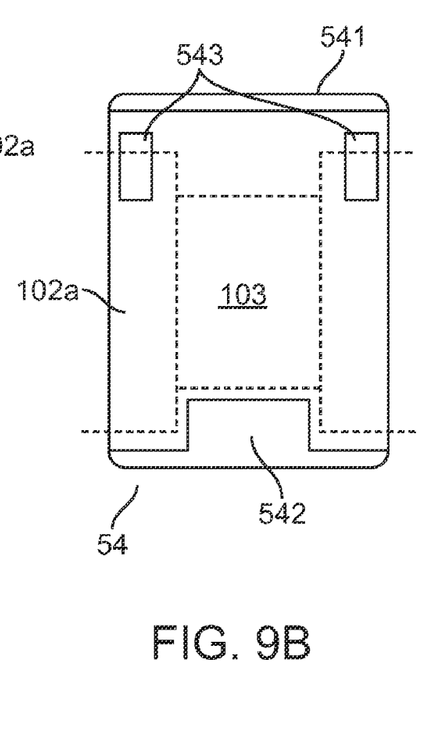

The tear-off band 137 shown in FIGS. 1-4 is not present on the device 10. In its place is a safety means 54 comprising a collar which fits around the cartridge 103 and the sleeve parts 102a, 102b. The construction of part 54 is shown in more detail in FIG. 9. As seen in FIG. 9A being a cross section through the collar 54 and device 10 at line A-A in FIG. 5, and FIG. 9B being a longitudinal part sectional view through the collar 54 and immediately adjacent part of device 10, at right angles to the line A-A of FIG. 9A, the part 54 comprises a collar 541 of cross sectional dimensions greater than that of sleeve parts of sleeve parts 102a, 102b. The part 54 has an obstructer part 542 being a block which when the part 54 is in place around the cartridge 103 as shown in FIG. 5 obstructs any relative longitudinal movement of sleeves 102a and 102b, by fitting longitudinally between them and blocking their relative movement. The collar 541 is supported in this configuration by resilient spring leaves 543, 544 which bear on the sleeve parts 102a, 102b. This is the first configuration of part 54.

Figure 6:
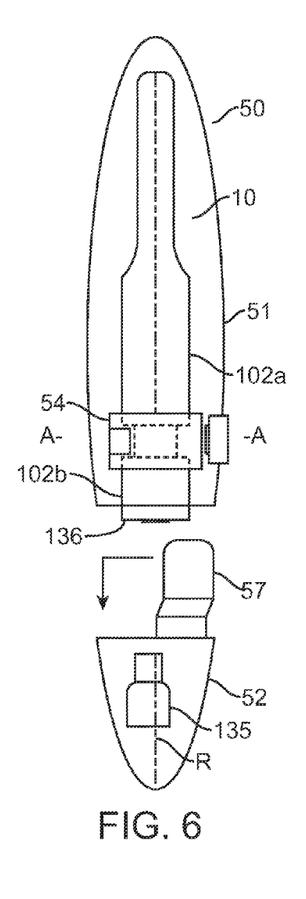

Referring to FIG. 6 the second casing part 52 has been rotated relative to the first casing part 51 about the axis of rotation R, thereby unscrewing second casing part 52 from first casing part 51 at screw connection 53 and disconnecting parts 51 and 52. Second casing part 52 has internal parts e.g. internal supports, walls etc. (not shown but the construction of which will be apparent), which bear upon the break-off tip 135. Axis R is parallel to but no co-axial with the longitudinal axis of the part 10, a shearing force is applied to the frangible joint 136, which consequently breaks. The device 10, is now in a configuration corresponding to FIG. 2.

Figure 7:
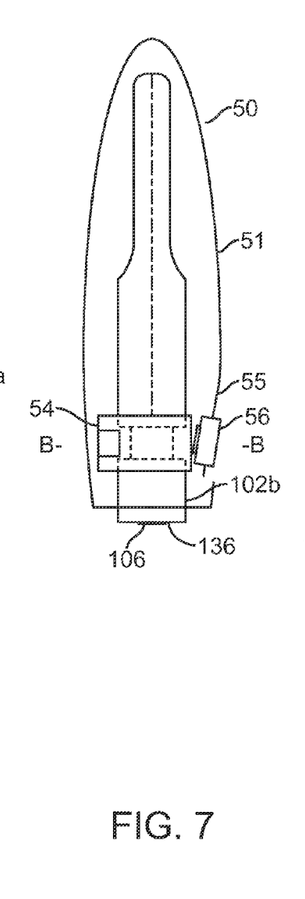
Figure 9C:
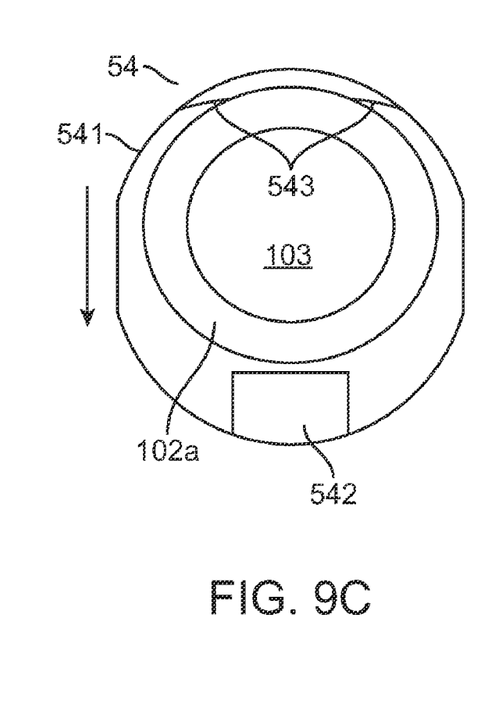

Referring to FIG. 7 an actuator means is provided by a resilient tongue 55, integral with first casing part 51, and which can be inwardly deflected by pressure on an operating button 56. This inward deflection causes button 56 to bear upon the upper surface (as seen in FIG. 9) of the collar 541, and the collar 541 to be consequently moved downwardly against the resilience of springs 543, and the obstructer part 542 to be consequently moved into a position in which it does not obstruct the relative movement of sleeve parts 102a and 102b. This is shown more clearly in FIG. 9C, being the second configuration of part 54. When in this second configuration the first casing part 51 and part 54 may have co-operating means, e.g. snap fit detent means, so that part 54 is retained in this second configuration independently of pressure applied by button 56. Alternatively, e.g. as a further safety feature, the casing may be constructed so that continued pressure on part 55 is necessary to hold part 54 in this second configuration. The device 10 is now in a configuration corresponding to FIG. 3.

Also as shown in FIGS. 5 and 6, the second casing part 52 integrally incorporates a cover part 57 comprising a cover flap which covers the actuator button 56 when the second casing part is attached by the screw thread 53 to first casing part 51. This prevents the actuator part 56 from being actuated in the manner shown in FIG. 7 until the second casing part 52 has been unscrewed from first casing part 51 and removed in the downward direction as shown, with the consequence of breaking off the break off tip 135, and thereby causes the user to operate the device 10 in the proper operating sequence as described with reference to FIGS. 1-4.

Figure 8:
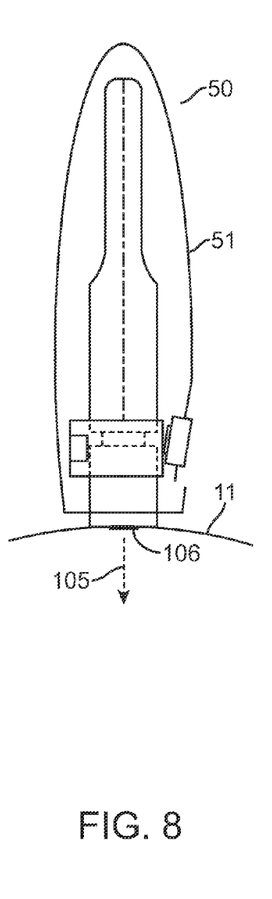

Referring to FIG. 8, the orifice 106 has been placed against the skin 11 of the user and pressure has been applied to the first casing part 51 in the direction toward the skin 11. Tis pressure is communicated to the injection device 10 to force sleeve part 102a downwardly relative to sleeve part 102b. In a manner corresponding to FIG. 4 this has caused the device 10 to "fire" and to inject medicament 105 through the user's skin 11.

Figure 10:
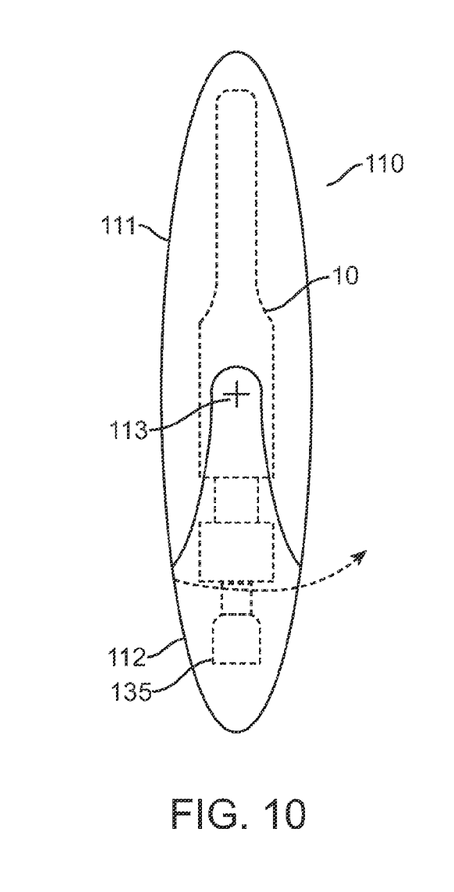
FIGS. 10 and 11 show schematically the construction of another casing of this invention and its operation with a device as shown in FIGS. 1-4.

Referring to FIG. 10, another casing 110 of this invention is shown in a side view. The casing 100 incorporates a device 10 as with the casing of FIGS. 5-9. The casing 100 comprises first casing part 111 and second casing part 112. The internal construction of the first casing part 111 is analogous to that of first casing part 51, i.e. incorporating a safety means 54 and an actuating means 55, 56 as therein.

Figure 11:
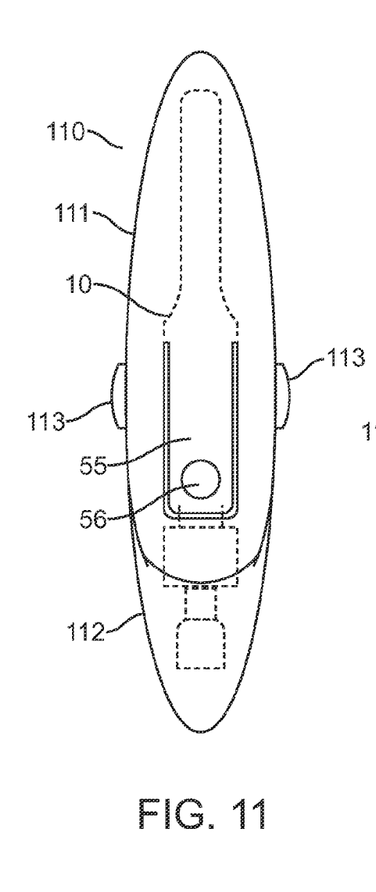

FIG. 11 shows a plan view of the casing 110 illustrating more clearly the construction of the part 55 and 56, which is analogous to those of FIGS. 5-9.

Figure 11A:
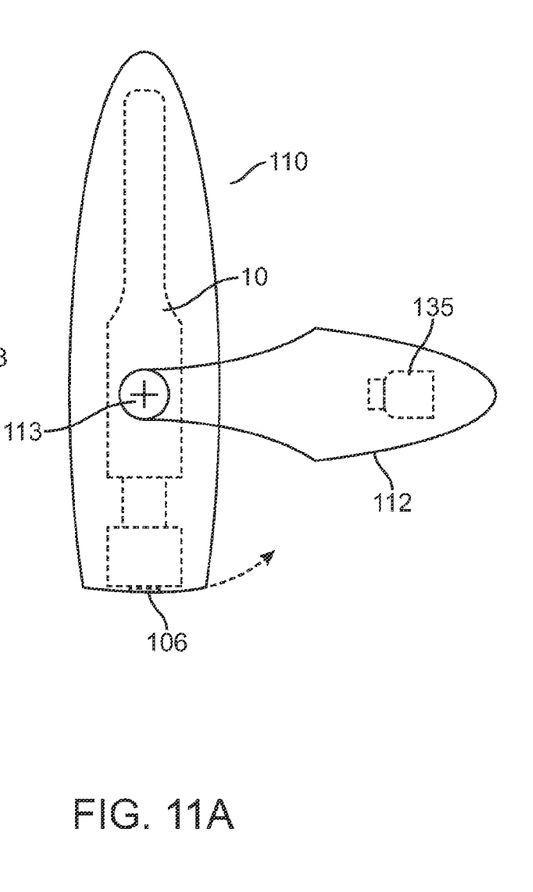

In the casing 110 the second casing part 112 is mounted on two opposite pivot axles 113, so that part 112 can rotate about the axis between these axles 113, this axis of rotation being perpendicular to the longitudinal axis of the device 10 and of the elongated casing 110, so that part 112 swings in rotation relative to part 111 and follows the arc shown in FIG. 10, to swing into the position shown in FIG. 11A. As the casing part 112 rotates in this way its internal parts (not shown), such as internal ribs or a cup-shaped holder to hold the break-off tip 135, bear upon the break-off tip 135 and cause the frangible joint 137 to shear analogously to FIGS. 2 and 6. As the part 112 continues to rotate along this arc, it carries the broken off tip 135 away from orifice 106. The casing parts 111, 112 may have respective co-operating locking means (not shown) by which the part 112 may be initially releasably locked in place in its non-rotated configuration as shown in FIG. 10 before being unlocked to allow the casing part 112 to swing through the arc. Such a locking means may help to prevent accidental break-off of the break off tip 135.

The actuator button 56 can then be operated in a manner analogous to the casing of FIGS. 5-9 to render the device 10 ready to trigger and operate.

The orifice 106 can then be placed against the user's skin 11 in a manner analogous to FIG. 8 and pressure can be applied to the first casing part 111 to force sleeve part 102a downwardly relative to sleeve part 102b causing the device 10 to "fire" as in FIGS. 4 and 8 to inject medicament 105 through the user's skin 11.

In the device of FIGS. 10 and 11 it is of course important that the arc which the second casing part 112 follows allows sufficient of the device 10 to project beyond the lower end as shown of the casing part 111 to allow the orifice 106 to be placed adjacent to the user's skin. This can be arranged by a suitable geometry of the casing 110 to give the second casing part 112 sufficient clearance of the orifice 106 as the part 112 swings in its arc. The second casing part 112 may also be constructed so that a downward (as shown) movement of the second casing part 112 is necessary before the second casing part 112 can pivot in the manner shown. This can be achieved for example by means of a "keyhole" shaped pivot socket which engages with an elongate section stub axle which can only rotate when the axle has been moved longitudinally into the wide part of the "keyhole". This can help to provide the clearance between the second casing part 112 and the orifice 106.

The dimensions of the casing parts 111 and 112 may be such that the second casing part 112 may rotate through 180° from the position shown in FIGS. 10 and 11 so that it can conveniently be "stowed" at the opposite end of the first casing part 111 to that from which the orifice 106 projects.

It will be apparent that the casing 51, 52, 101, 102 facilitates the operation of the device 10, and as seen in FIG. 11 can enhance the outward appearance of the casing.

Figure 12:
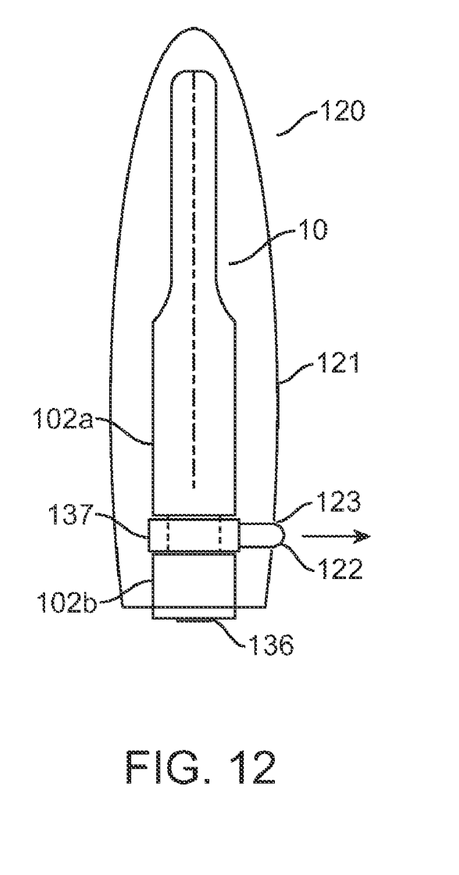
FIGS. 12 and 13 show schematically the construction of another casing of this invention and its operation with a device as shown in FIGS. 1-4.
Figure 13:
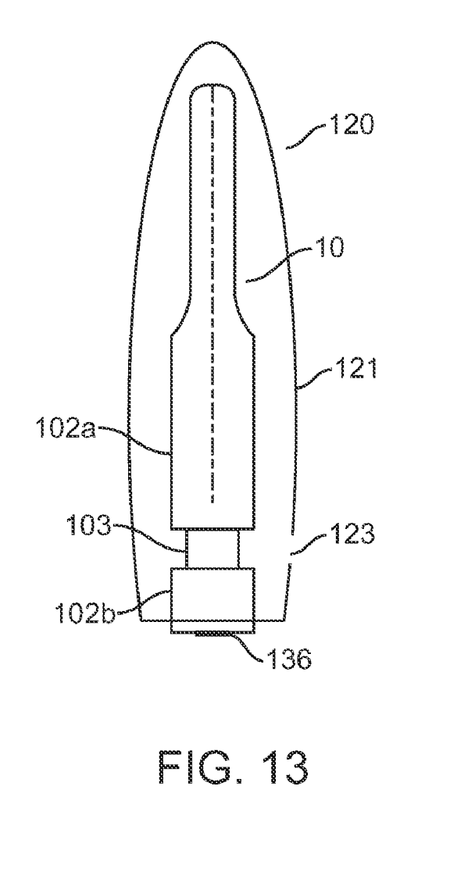

Referring to FIGS. 12 and 13 another casing 120 is shown in schematic longitudinal section. The casing 120 is similar in construction to that of FIGS. 5-8, having a first casing part 121, and a second casing part (not shown) which is identical to that 52 of FIGS. 5-8 and which is initially connected to casing part 121 by a screw thread in an analogous manner. In FIG. 12 the casing 120 is shown with this second casing part removed, i.e. in a configuration analogous to FIG. 7.

The casing 120 incorporates a device 10 as shown in FIGS. 1-4. The device 10 has a safety means being a tear-off band 137 analogous to that shown in FIGS. 1 and 2. The band 137 has an extension 122 which extends through a window aperture 123 in first casing part 121 to the outside of casing part 121. The extension 122 may be gripped by a user and pulled from outside the casing to thereby remove the band 137 as seen in FIG. 13. The casing 120 is then in a configuration analogous to FIG. 7 and may be used in a manner analogous to FIG. 8. It will be appreciated that band 137 in FIG. 12 may be replaced by other forms of removable obstructer means. As in FIGS. 5-8 a cover part such as that 57 may cover the extension 122 until the second casing part has been removed.

Figure 14:
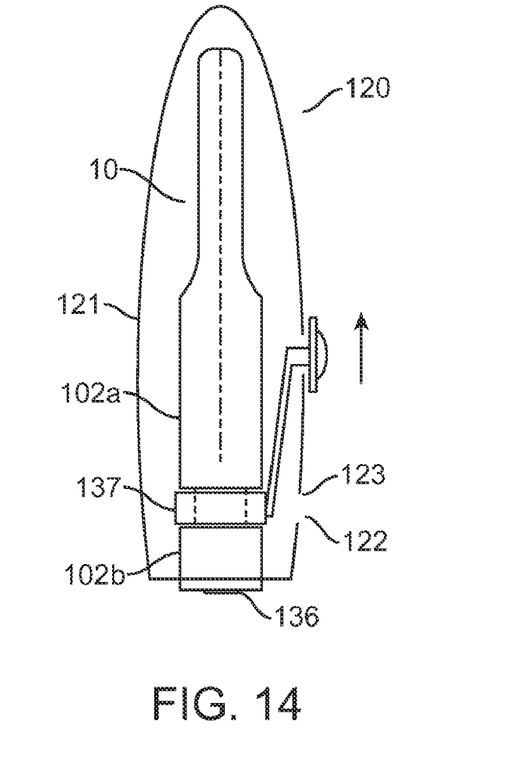
FIGS. 14 and 15 show schematically the construction of another casing of this invention and its operation with a device as shown in FIGS. 1-4.
Figure 15:
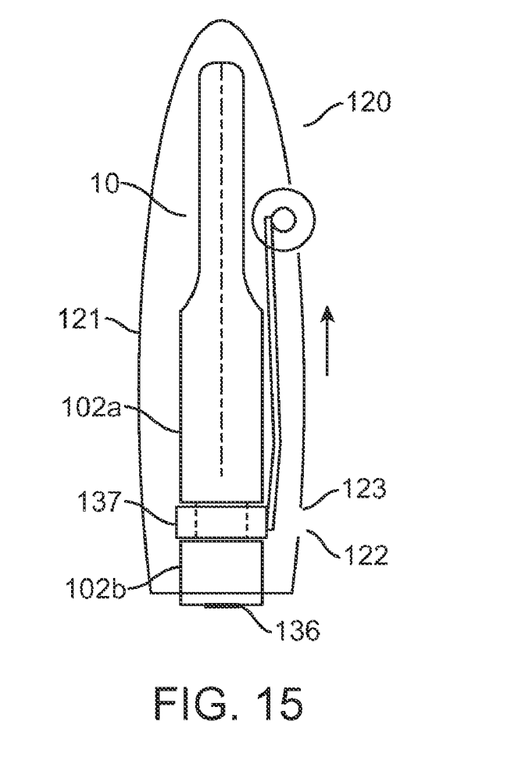

Referring to FIGS. 14 and 15, these illustrate casings 140, 150 similar in general concept to FIGS. 12 and 13, and corresponding parts are numbered correspondingly, but in which the actuator means may comprise a means to apply a pulling force to the safety means to pull the safety means from its first configuration into its second configuration.

In FIG. 14 the actuator means 141 comprises a slider 141 e.g. in the form of a slider button, easy for the user to access and use, slideably moveable relative to the casing 140. For example the slider may be mounted in a slide groove or track (not shown) in the wall of the casing 140. The slider 141 is connected e.g. integrally to a connector means 142 connecting the slider 141 to the safety means 137. The user can move the slider 141 to pull the safety means 137, and this can cause the safety means to be pulled from its first configuration (as shown in FIG. 14) into its second configuration e.g. analogous to FIG. 13. For example the safety means 137 may comprise a plastics material strip which can be unwound from its position around the device 10.

In FIG. 15 the actuator means 151 comprises a pulley wheel, rotatably moveable e.g. by being mounted on an axle (not shown) relative to the casing 150 and which can easily be rotated by the user, e.g. by a thumb operation. There is a connector means 152 connecting the pulley wheel 151, e.g. an integral construction, to the safety means 137 whereby the user can rotate the pulley wheel 151 to pull the safety means from its first configuration (as shown in FIG. 15) into its second configuration e.g. analogous to FIGS. 1-4.

Figure 16:
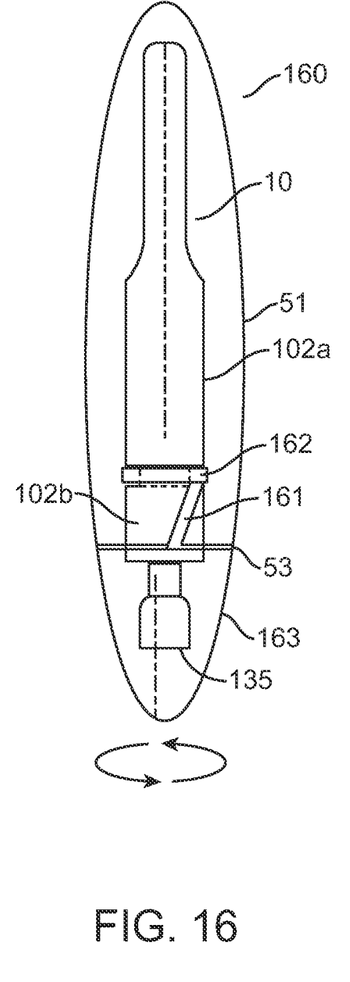
FIGS. 16 and 17 show schematically the construction of another casing of this invention and its operation with a device as shown in FIGS. 1-4.
Figure 17:
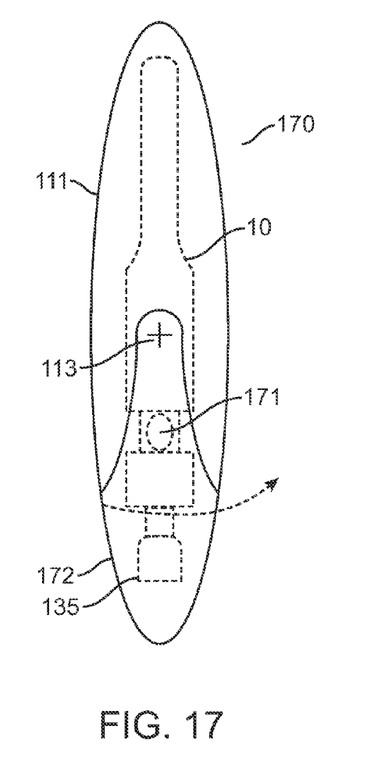
Figure 17A:
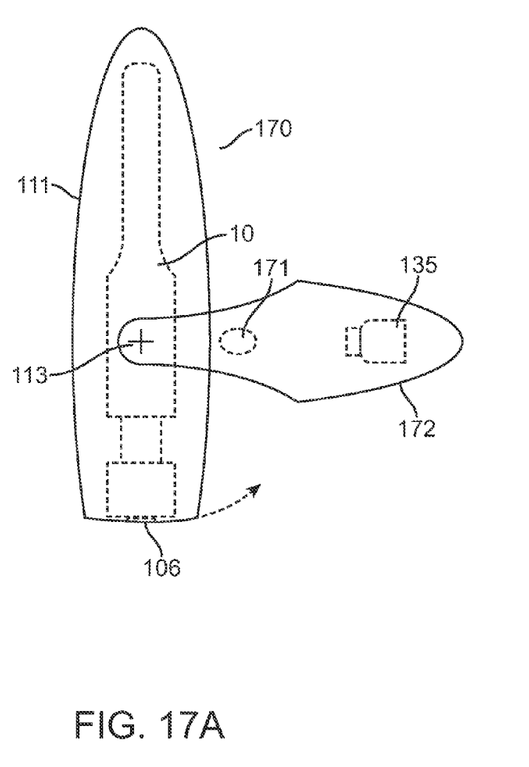

Referring to FIGS. 16 and 17, these illustrate casings similar in concept to FIGS. 10-11 and FIGS. 5-8, corresponding parts of which are numbered correspondingly, but in which the second casing part 163 or 172 comprises the actuator means 161, or safety means 171, so that the movement of the second casing part 163 or 172 relative to the first casing part 111, 51 causes the safety means 162, 171 of an injector device 10 enclosed within the casing 160, 170 to move from its first configuration to its second configuration.

Figure 16A:
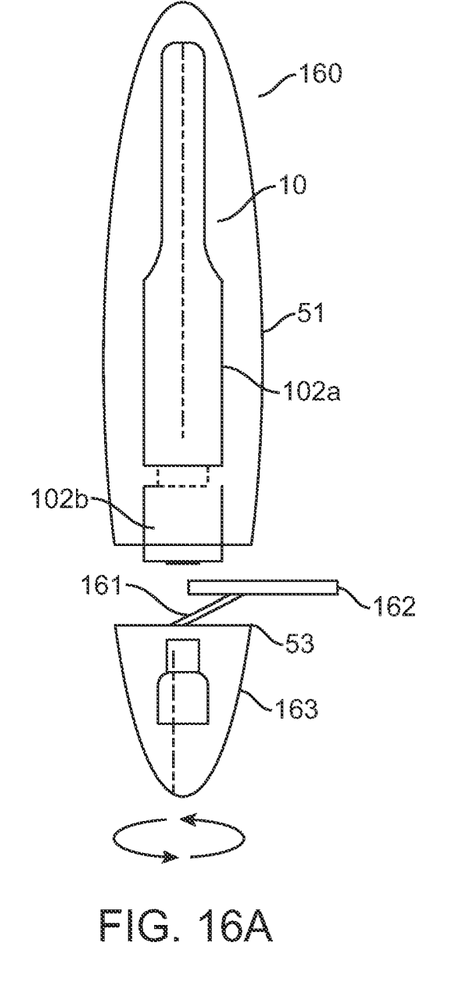

In FIG. 16 the second casing part 163 comprises a bearing part 161 in the form of plastics connector strip 161 which may be integrally made with the tear-off band 162 which comprises a safety means analogous in operation to that 137 of FIG. 12. When the second casing part 163 is rotated to unscrew casing part 163 from first casing part 51, the bearing part 161 bears upon the safety means 162 by pulling the safety means 162 and unwinding safety means 162 from the device 10 enclosed therein, as shown in FIG. 16A. Consequently the break-off tip 135 is first broken off as second casing part 163 rotates, then the safety means 162 functions to allow the trigger of the device 10 to operate in a manner analogous to that above.

In FIG. 17 the second casing part 172 itself comprises a safety means. The second casing part 172 incorporates at least one obstructer part 171, projecting inwardly toward the device 10 enclosed therein. In its first configuration as shown in FIG. 17 the obstructer part 171 functions to obstruct relative movement of the trigger parts 102a, 102b of the device 10 as shown in FIGS. 1-4. As second casing part 172 swings in an arc about the pivot axis 113, the second casing part 172 firstly breaks off the break-off tip in a manner analogous to FIGS. 10 and 11, and then as second casing obstructer part 171 moves out of its obstructing position between the upper sleeve part 102a, and lower sleeve part 102b. The first casing part 170 may be made with suitable clearances etc. to allow the movement of the obstructer part 171.

Figure 18:
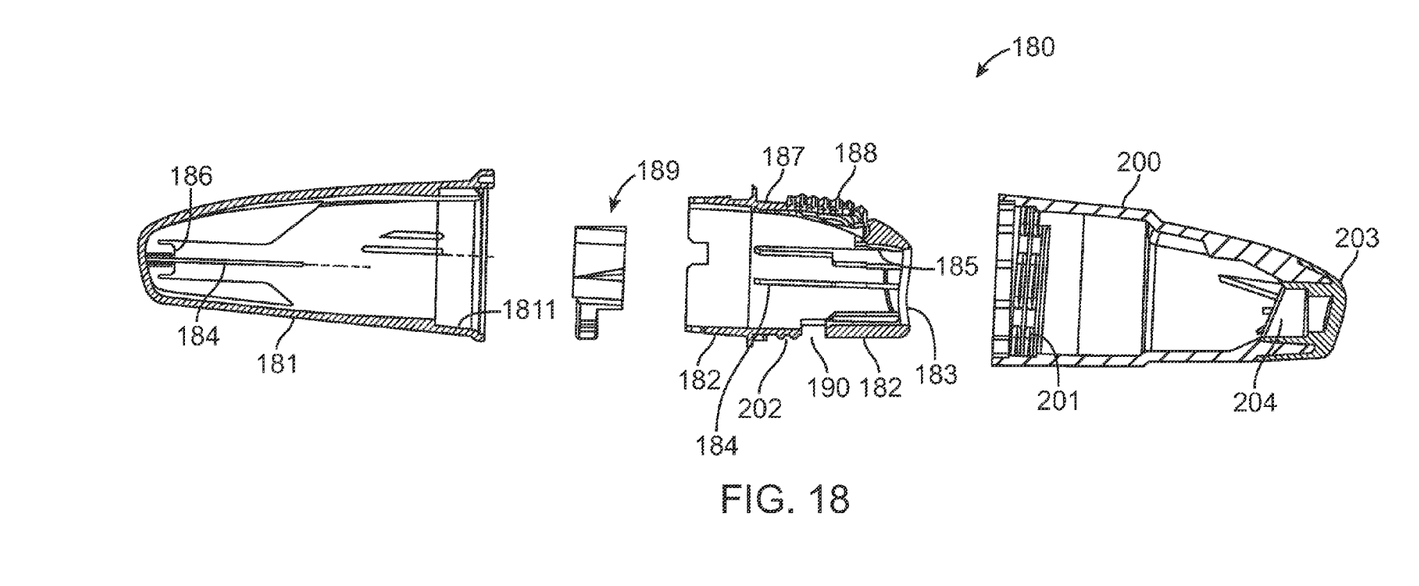
FIG. 18 shows a casing of this invention, in multi-part construction.

Referring to FIG. 18, a casing 180 is shown in a dissembled view. The casing 180 is generally similar in construction and operation to that shown in FIGS. 5-8 as will be apparent.

Referring to FIG. 18 a casing 180 of this invention is shown in a longitudinal sectional view. The casing 180 is of multipart construction for example comprising a first casing sub-part 181 and a second casing sub-art 182 which fit together by a tight friction or snap-fit fit of plug part 1811 of part 181. When fitted together the parts 181 and 182 define an elongate casing which can enclose an injection device (not shown) of the general type 10 described above, with its break-off tip 135 projecting through an end opening 183 of part 182. The casing sub-parts 181, 182 are shaped internally and are provided with internal support ribs 184 to hold the device 10 non-rotatably within the assembled casing 181, 182. Internally the part 182 has a conical interior at 185. The device 10 has a corresponding conical outer profile which can abut against this internal conical profile 185, and there is also an end support 186 against which a device 10 within the casing assembly 181, 182 can abut, and these features prevent longitudinal movements of the device 10.

Casing sub-part 182 incorporates an actuator means 187, 177 similar in construction to that 56, 57 of FIG. 7. The actuator means comprises a resilient tongue 187, integral with sub-part 182, an which can be inwardly deflected by pressure on an operating button 188.

Figure 18A:
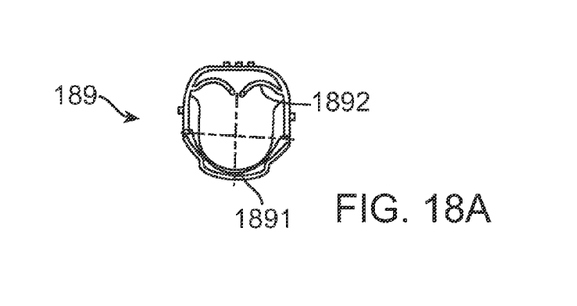
Figure 18B:
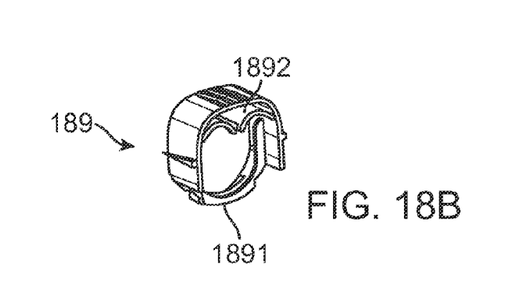

Located within sub-part 182 is a collar 189, similar in overall construction to that described with references to FIG. 9. Collar 189 is shown in a longitudinal view in FIG. 18A and in perspective view in FIG. 18B. Corresponding to FIG. 9 the collar 189 comprises an obstructer part 1891 and resilient spring leaves 1892. The operation of the collar 189 under the action of the actuator means 187, 188 is analogous to collar 541 of FIG. 9. However as an additional feature the sub-part 182 is provided with a cut out 190 into which the obstructer part 1891 may fit when the collar 189 is displaced in the downward direction as seen, so that the obstructer part 1891 can be seen therein as a confirmation that the device has been properly operated.

The casing assembly 181, 182 comprises a first casing part. The casing 180 also has a second casing part 200, in the form of a generally rounded conical cover into which the sub-part 182 fits and engages by means of co-operating screw threads 201, 202. The casing part 200 has a nose cone 203 which is made of a high-friction elastomer material which can grip the break-off tip 135 of a device 10 enclosed in first casing 181, 182, the nose cone 203 being shaped internally concave so that the break off tip 135 can comfortably fit into the conforming concavity 204.

In a construction and operation analogous to FIGS. 5 and 6, the second casing part 200 can be rotated relative to first casing part 181, 182, about an axis of rotation thereby unscrewing second casing part 200 from first casing sub-part 182 at screw connection 201, 202, thereby disconnecting parts 181, 182 from second casing part 200. Second casing part 200 is constructed such that the concavity 204 is not concentric with the axis of rotation, so that as second casing part 200 rotates about this axis the nose cone 203 is displaced transverse to the rotation axis and bears upon the break-off tip 135. A shearing force is consequently applied to the frangible joint 136, which consequently breaks, in a manner analogous to FIG. 6.

The second casing part 200 is also constructed so that as it fits over sub-part 182, casing part 200 covers actuator means 187, 188 so that the actuator means 187, 188 is shielded from being actuated until casing part 200 has been unscrewed and removed, thereby first breaking off the break-off tip 135 and therefore causing device 10 to be operated in the correct operating sequence.

The invention claimed is:

1. A needleless injection device, comprising
a casing;
a cartridge containing a medicament for injection and an orifice at one end thereof through which the medicament is driven for injection through a patient's skin;
a drive mechanism which upon actuation applies force to the medicament, forcing the medicament out of the orifice and through the patient's skin;
a trigger mechanism which actuates the drive mechanism;
a safety mechanism which, in a first configuration, prevents the trigger mechanism from actuating the drive mechanism and in a second configuration allows trigger mechanism to actuate the drive mechanism; and
an actuator lever which moves the safety mechanism from its first configuration into its second configuration;
wherein the actuator lever comprises a portion extending outside of the casing which portion is accessible to a user and which portion is comprised of a component configured such that when the portion is moved by the user the component applies a pulling force to the safety mechanism to pull the safety mechanism into its second configuration.

2. The device of claim 1, wherein the safety mechanism in its first configuration prevents the trigger mechanism from moving.

3. The device of claim 1, further comprising:
a retaining mechanism which retains the safety mechanism of an enclosed injection device in its second configuration after the safety mechanism has been brought into its second configuration.

4. The device of claim 2, wherein the safety mechanism comprises an obstructer portion which in the first configuration obstructs, and in the second configuration allows, movement of the trigger mechanism.

5. The device of claim 4, wherein the safety mechanism comprises a collar shaped to surround a portion of the injection device, the collar is moveable from its first collar configuration into its second collar configuration in a direction generally perpendicular to a direction in which the medicament exits the orifice, the collar comprising an obstructer portion.

6. The device of claim 5, wherein the trigger mechanism is comprised of two moveable upper and lower sleeve portions which on relative movement allow the drive mechanism to act, and the safety mechanism comprises an obstructer portion which in its first configuration obstructs, and in its second configuration allows, the relative movement of the sleeve portions.

7. The device of claim 6, wherein the safety mechanism comprises an obstructer portion which is brought from its first configuration to its second configuration by a movement of the obstructer portion in a direction perpendicular to a direction of relative movement of the two sleeve portions.

8. A combination comprising:
a casing which partially encloses a needleless injection device;
wherein the needleless injection device comprises:
a cartridge containing a medicament for injection and an orifice at one end thereof through which the medicament is driven for injection through a patient's skin;
a drive mechanism which upon actuation applies force to the medicament, forcing the medicament out of the orifice and through the patient's skin;
a trigger mechanism which actuates the drive mechanism;
a safety mechanism which, in a first configuration, prevents the trigger mechanism from actuating the drive mechanism, and, in a second configuration, allows the trigger mechanism to actuate the drive mechanism; and a break-off tip which encloses the cartridge orifice prior to being broken off, the break-off tip configured such that breaking off the break-off tip irreversibly exposes an actuator for the safety mechanism.

9. The combination of claim 8, wherein the casing may be broken off to provide for sequential operation of the needleless injection device.

10. The combination of claim 9, wherein the sequential operation provides for (a) breaking off the break-off tip; and (b) placing the safety mechanism in the second position.

11. The combination of claim 10, wherein the casing comprises moveable first and second casing components, a first casing component adapted to hold the injection device, and a second casing component adapted to bear upon the break-off tip as a result of relative motion of the first and second components to apply a force thereto causing the break-off tip to break off from an injection device enclosed within the casing.

12. The combination of claim 11, wherein the first casing component is elongated with an opening at a first end.

13. The combination of claim 12, wherein the first casing component is elongated along a longitudinal axis, and wherein the second casing component is designed to apply a rotary motion relative to the first portion so as to bear on the break-off tip of a container held by the first casing portion, and to apply a twisting shearing force to the frangible joint between the break-off tip and the container.

14. The combination of claim 13, wherein the rotary motion is chosen from:
    transverse to the longitudinal axis;
    perpendicular to this longitudinal axis;
    coaxial with the longitudinal axis;
    about a rotation axis parallel to but non-coaxial with this longitudinal axis;
    about a rotation axis at a non-zero angle to the longitudinal axis.

15. The combination of claim 14, wherein the rotary motion is about a rotation axis at a non-zero angle to the longitudinal axis.

16. The combination of claim 11, wherein the second casing component comprises a cover portion over the actuator for the safety mechanism which prevents operation of the actuator for the safety mechanism until the cover portion is removed.

17. The combination of claim 9, wherein the actuator for the safety mechanism moves the safety mechanism from its first configuration to its second configuration.

18. The combination of claim 17, wherein the actuator moves the safety mechanism from its first configuration to its second configuration by pulling.

19. The combination of claim 18, wherein the safety mechanism comprises an obstructer portion which functions to obstruct movement of a portion of the injection device which is essential for operation.

20. The injection device of claim 1, wherein the drive mechanism comprises a compressed gas cylinder.

21. The combination of claim 8, wherein the casing comprises a first casing sub-part and a second casing sub-part which fit together by a method chosen from, a tight friction fit, and a snap-fit fit.

22. A needleless injector device, comprising:
    a cartridge containing a medicament for injection and an orifice at one end thereof through which the medicament is driven for injection through a patient's skin;
    a drive mechanism which upon actuation applies force to the medicament, forcing the medicament out of the orifice and through the patient's skin;
    a trigger mechanism which actuates the drive mechanism;
    a safety mechanism which in a first configuration prevents movement of the trigger mechanism and in a second configuration allows movement of the trigger mechanism; and
    a casing which encloses the drive mechanism, the casing comprising a break-off tip configured such that breaking off the break-off tip irreversibly exposes both the safety mechanism and the orifice through which the medicament is driven for injection through a patient's skin.

23. A needleless injection device, comprising
    a casing;
    a cartridge containing a medicament for injection and an orifice at one end thereof through which the medicament is driven for injection through a patient's skin;
    a drive mechanism which upon actuation applies force to the medicament, forcing the medicament out of the orifice and through the patient's skin;
    a trigger mechanism which actuates the drive mechanism;
    a safety mechanism which, in a first configuration, prevents the trigger mechanism from actuating the drive mechanism and in a second configuration allows the trigger mechanism to actuate the drive mechanism;
    a retaining mechanism which retains the safety mechanism of an enclosed injection device in its second configuration after the safety mechanism has been brought into its second configuration; and
    an actuator lever which moves the safety mechanism from its first configuration into its second configuration;
    wherein the actuator lever comprises a portion extending outside of the casing which portion is accessible to a user and which when the portion is moved by the user the movement brings the safety mechanism into its second configuration.

24. The device of claim 23, wherein the safety mechanism in its first configuration prevents the trigger mechanism from moving.

25. The device of claim 23, wherein the actuator lever is comprised of a component which applies a pulling force to the safety mechanism to pull the safety mechanism from its first configuration into its second configuration.

26. The device of claim 25, wherein the safety mechanism comprises an obstructer portion which in the first configuration obstructs, and in the second configuration allows, movement of the trigger mechanism.

27. The device of claim 26, wherein the safety mechanism comprises a collar shaped to surround a portion of the injection device, the collar is moveable from its first collar configuration into its second collar configuration in a direction generally perpendicular to a direction in which the medicament exits the orifice, the collar comprising an obstructer portion.

28. The device of claim 27, wherein the trigger mechanism is comprised of two moveable upper and lower sleeve portions which on relative movement allow the drive mechanism to act, and the safety mechanism comprises an obstructer portion which in its first configuration obstructs, and in its second configuration allows, the relative movement of the sleeve portions.

29. The device of claim 28, wherein the safety mechanism comprises an obstructer portion which is brought from its first configuration to its second configuration by a movement of the obstructer portion in a direction perpendicular to a direction of relative movement of the two sleeve portions.

* * * * *